(12) United States Patent
Sathaye et al.

(10) Patent No.: US 7,680,536 B2
(45) Date of Patent: Mar. 16, 2010

(54) CAPTURE THRESHOLD ESTIMATION FOR ALTERNATE PACING VECTORS

(75) Inventors: Alok S. Sathaye, Minneapolis, MN (US); Jason M. Brooke, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 815 days.

(21) Appl. No.: 11/505,645

(22) Filed: Aug. 17, 2006

(65) Prior Publication Data

US 2008/0046019 A1   Feb. 21, 2008

(51) Int. Cl.
*A61N 1/362* (2006.01)
(52) U.S. Cl. .............................. 607/28; 607/8; 600/512
(58) Field of Classification Search .................. 607/8, 607/28; 600/512
See application file for complete search history.

(56) References Cited

U.S. PATENT DOCUMENTS

| 6,076,015 | A | 6/2000 | Hartley et al. |
| 6,243,606 | B1 * | 6/2001 | Mann et al. .................... 607/14 |
| 6,684,101 | B2 | 1/2004 | Daum |
| 6,760,624 | B2 | 7/2004 | Anderson et al. |

* cited by examiner

*Primary Examiner*—Carl H Layno
*Assistant Examiner*—Yun Haeng Lee
(74) *Attorney, Agent, or Firm*—Hollingsworth & Funk, LLC

(57) ABSTRACT

Approaches for estimating capture thresholds for alternate pacing vectors of multi-electrode pacing devices are described. Capture thresholds of at least one initial pacing vector is measured. The impedance of the initial pacing vector and at least one alternate pacing vector is measured. The initial and alternate pacing vectors have an electrode in common. The common electrode has the same polarity in both the initial and the alternate pacing vectors. The capture threshold for the alternate pacing vector may be estimated based on the measured capture threshold of the initial pacing vector, the measured the impedance of the initial pacing vector, and the measured impedance of the alternate pacing vector.

30 Claims, 7 Drawing Sheets

CAPTURE THRESHOLD ESTIMATION FOR ALTERNATE PACING VECTORS

FIELD OF THE INVENTION

The present invention relates generally to cardiac devices and methods, and, more particularly, to capture threshold estimation for alternate pacing vectors based on measured capture threshold and impedance values.

BACKGROUND OF THE INVENTION

When functioning normally, the heart produces rhythmic contractions and is capable of pumping blood throughout the body. The heart has specialized conduction pathways in both the atria and the ventricles that enable excitation impulses (i.e. depolarizations) initiated from the sino-atrial (SA) node to be rapidly conducted throughout the myocardium. These specialized conduction pathways conduct the depolarizations from the SA node to the atrial myocardium, to the atrioventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver stimulation to the heart in accordance with various therapies for treating cardiac arrhythmias and dysynchronies.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to "capture" the heart tissue by generating a propagating depolarization wave that results in a contraction of the heart chamber. It is desirable for a pace pulse to have sufficient energy to stimulate capture of the heart chamber without expending energy significantly in excess of the capture threshold. Thus, accurate determination of the capture threshold is required for efficient pace energy management. If the pace pulse energy is too low, the pace pulses may not reliably produce a contractile response in the heart chamber and may result in ineffective pacing. If the pace pulse energy is too high, the patient may experience discomfort and the battery life of the device will be shorter.

Detecting if a pacing pulse captures the heart allows the pacemaker to adjust the energy level of pace pulses to correspond to the optimum energy expenditure that reliably produces capture. Further, capture detection allows the pacemaker to initiate a back-up pulse at a higher energy level whenever a pace pulse does not produce a contraction.

Devices for cardiac pacing and sensing may utilize a number of electrodes electrically coupled to the heart and configured to sense and/or pace a heart chamber. Pacing via multiple intra-chamber electrode pairs may be beneficial, for example, to stimulate the heart tissue in a coordinated sequence that improves contractile function of the heart chamber. It is desirable to determine the energy required to capture the heart tissue for each set of electrodes used for pacing. The present invention provides methods and systems for estimating capture thresholds and provides various advantages over the prior art.

SUMMARY OF THE INVENTION

The present invention involves approaches for estimating capture threshold values. One embodiment of the invention is directed to a method for estimating capture thresholds for one or more alternate pacing vectors. A capture threshold of at least one initial pacing vector is measured. The impedances of the at least one initial pacing vector and the at least one alternate pacing vector are measured. The at least one initial pacing vector and the at least one alternate pacing vector have an electrode in common, the common electrode having the same polarity in both the initial and alternate vectors. The capture threshold of the at least one alternate pacing vector is estimated based on the measured capture threshold of the at least one initial pacing vector, the measured impedance of the at least one initial pacing vector, and the measured impedance of the at least one alternate pacing vector.

According to one aspect of the invention, the capture threshold of a single alternate pacing vector may be estimated based on measured capture thresholds of multiple initial pacing vectors. According to another aspect of the invention, capture thresholds for multiple alternate pacing vectors may be estimated based on the measured capture threshold of a single initial pacing vector. In yet another aspect, multiple alternate pacing vectors may be estimated based on measured capture thresholds of multiple initial pacing vectors.

In one implementation, estimation of the capture threshold may involve estimating based on a most recent measurement of the initial vector capture threshold, a most recent measurement of the initial vector impedance, and/or a most recent measurement of the impedance of the alternate vector. According to one implementation, the capture threshold may be estimated based on an average value of multiple measurements of the initial vector capture threshold, an average value of multiple measurements of the initial vector impedance, and/or an average value of multiple measurements of the impedance of the alternate vector.

The estimation of the alternate vector capture threshold may be based on an equal relationship between a capture threshold current of the initial vector and a capture threshold current of the alternate vector. The relationship between the threshold currents of the initial and alternate vectors may be assumed to be constant, piecewise linear, or non-linear, for example.

In a further aspect, the method provides for disabling pacing under certain circumstances. If a possible error in at least one of the measured values used for the capture threshold estimation is detected, an appropriate action may be taken, for example, disabling pacing via the alternate vector, modifying the pacing output to the alternate vector to a high output state, such as the device pacing at the maximum output parameters, and/or providing notice to a physician such as through an alert transmitted to an external programmer or advanced patient management system server.

Another embodiment of the invention is directed to a cardiac rhythm management system capable of providing capture threshold estimation. The system includes electrodes electrically coupled to the heart, each pair of the electrodes forming an initial pacing vector or an alternate pacing vector. Capture threshold measurement circuitry is configured to measure a capture threshold of at least one initial pacing vector. Impedance measurement circuitry is configured to measure an impedance of the at least one initial pacing vector and an impedance of at least one alternate pacing vector. The at least one initial pacing vector and the at least one alternate pacing vector have an electrode in common. The common electrode is has the same polarity in both the at least one initial pacing vector and the at least one alternate pacing vector. A capture threshold estimation processor estimates a capture threshold for the at least one alternate pacing vector based on the measured capture threshold of the at least one initial pacing vector, the measured impedance of the at least one initial pacing, and the measured impedance of the at least one alternate pacing.

In various implementations, the initial pacing vector may include a left ventricular electrode, a right ventricular electrode, a right atrial electrode, or a left atrial electrode. The alternate pacing vector may include a left ventricular electrode, a right ventricular electrode, a right atrial electrode, or a left atrial electrode.

According to one aspect of the system, the capture threshold estimation processor is configured to estimate the capture threshold for the alternate pacing vector based at least in part on one or more of a most recent measurement of the capture threshold of the initial electrode pair, a most recent measurement of the initial electrode pair impedance and a most recent measurement of the alternate electrode pair impedance. According to another aspect, the capture threshold estimation processor is configured to estimate the capture threshold of the alternate pacing vector based at least in part on an average value of at least one of multiple capture threshold measurements of the initial pacing vector, multiple impedance measurements of the initial pacing electrode, and multiple impedance measurements of the alternate pacing vector.

For example, the threshold estimation may be based on an equal relationship between a capture threshold current of the initial pacing vector and a capture threshold current of the alternate pacing vector, a constant relationship between a capture threshold current of the initial pacing vector and a capture threshold current of the alternate pacing vector, a piecewise linear relationship between a capture threshold current of the initial pacing vector and a capture threshold current of the alternate pacing vector, or a non-linear relationship between a capture threshold current of the initial pacing vector and a capture threshold current of the alternate pacing vector.

The system may further include a therapy control processor configured to detect a possible error in at least one of the measured capture threshold of the initial electrode pair, the measured impedance of the initial electrode pair, and the measured impedance of the alternate electrode pair. The therapy control processor may modify pacing via the alternate electrode pair and/or generate an alert responsive to the detected possible error.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
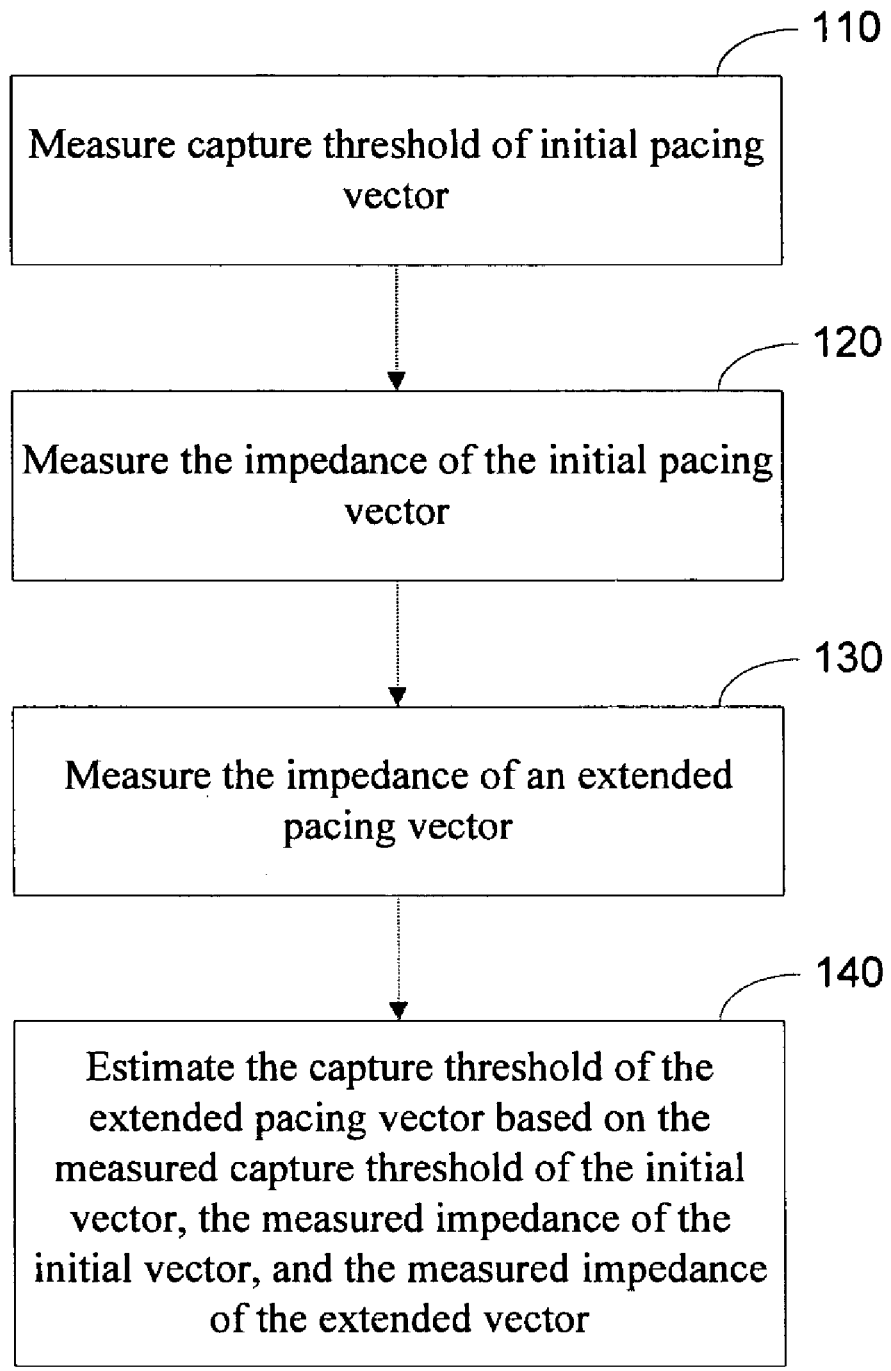
FIG. 1 is a flowchart illustrating a method of estimating the capture threshold of an alternate pacing vector in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

In multi-electrode pacing systems, multiple pacing electrodes may be disposed in a single heart chamber and/or in multiple heart chambers. Electrodes used for delivery of pacing pulses may include one or more cathode electrodes and one or more anode electrodes. Pacing pulses are delivered via the cathode/anode electrode pairs, where the term "electrode pair" denotes that at least one cathode electrode and at least one anode electrode are used. An electrode pair may involve more than two electrodes, such as when multiple electrodes that are electrically connected are used as the anode and/or multiple electrodes that are electrically connected are used as the cathode. Typically, pacing energy is delivered to the heart tissue via the cathode electrode(s) with a return path provided via the anode electrode(s). If capture occurs, the energy injected at the cathode electrode site creates a propagating wavefront of depolarization which may combine with other depolarization wavefronts to trigger a contraction of the cardiac muscle. The cathode and anode electrodes that deliver the pacing energy define the pacing vector used for pacing.

Pacing pulses may be applied through multiple electrodes (i.e., pacing vectors) in a single cardiac chamber in a timed sequence during the cardiac cycle to improve contractility and enhance the pumping action of the heart chamber. It is desirable for each pacing pulse delivered via the multiple pacing vectors to capture the cardiac tissue proximate the cathode electrode. The pacing energy required to capture the heart is dependent on the vector used for pacing. Particularly in the left ventricle, the energy required for capture, denoted the capture threshold, may be highly pacing vector dependent.

The capture threshold for a particular pacing vector may be determined by a capture threshold test. For example, the capture threshold test may step down the pacing energy for successive pacing cycles until loss of capture is detected. In other implementations, the capture threshold test may involve a step-up capture threshold test, a binary search test, or may involve other capture threshold testing methods as are known in the art. The capture threshold of a pacing vector may change over time due to various physiological effects. Testing the capture threshold for a particular pacing vector may be implemented periodically or on command to ensure that the pacing energy delivered to the particular pacing vector remains sufficient to produce capture.

In systems that use multiple pacing vectors, individually testing the capture threshold for each pacing vector may not be possible or desirable due to device limitations and/or time considerations, for example. According to the approaches of the present invention, the capture threshold of a pacing vector, referred to herein as an alternate pacing vector, may be estimated based on the measured capture threshold of a pacing vector sharing a common electrode having the same polarity (anode or cathode) with the alternate vector. The pacing vector used to estimate the capture threshold of the alternate vector is referred to herein as the initial pacing vector.

In some implementations, for example, those having a need for higher accuracy in the estimation of the alternate pacing vector capture threshold, the capture threshold of the alternate pacing vector may be estimated based on capture threshold measurements and/or impedance measurements of multiple initial vectors. For example, the capture threshold and/or impedance measurements acquired from multiple initial vectors may be combined using any combination method, such as averaging, to determine a combined initial vector capture threshold and/or a combined initial vector impedance. These average values may be used, along with the impedance of the alternate vector, to determine the estimated capture threshold of the alternate vector.

In yet other implementations, multiple capture threshold measurements and/or multiple impedance measurements may be acquired from one or more initial vectors. These measurements may be averaged or otherwise combined and may be used along with an average of multiple impedance measurements of the alternate vector to estimate the capture threshold of the alternate vector.

The flowchart of FIG. 1 illustrates a process for estimating the capture threshold of an alternate pacing vector. Although this method is described in terms of capture threshold and impedance measurements from an initial vector, it will be understood that the estimation of the alternate vector capture threshold may be based on multiple measurements of the initial vector and/or measurements of multiple initial vectors.

The capture threshold of an initial pacing vector sharing a common electrode with the alternate pacing vector is measured 110. The common electrode has the same polarity for both the initial and alternate vectors. The capture threshold of the initial vector may be measured periodically during capture threshold tests.

The impedance of the initial pacing vector and the impedance of the alternate pacing vector are measured 120, 130. The impedance of a pacing vector involves resistance in the leads coupling the electrodes to the pulse generator, which is due in part to the surface area and the geometry of the electrodes, and the impedance associated with the conduction of the pulse through the body's tissues.

Any method for determining impedance for the vector may be used. One illustrative example of techniques and circuitry for determining the impedance of a pacing vector is described in commonly owned U.S. Pat. No. 6,076,015 which is incorporated herein by reference in its entirety, including its description of performing impedance measurements.

In accordance with this approach, measurement of impedance involves an electrical stimulation source, such as an exciter. The exciter delivers an electrical excitation signal, such as a strobed sequence of current pulses or other measurement stimuli, to the heart between the electrodes of a vector. In response to the excitation signal provided by exciter, a response signal, e.g., voltage response value, is sensed by impedance detector circuitry. From the measured voltage response value and the known current value, the impedance of the vector may be calculated.

Another method for determining the impedance of a pacing vector is to measure the output voltage at two points in time during the delivery of a pace pulse via the pacing vector. The pacing voltage in CRM devices is typically stored on a capacitor that partially discharges during the delivery of the pacing pulse. Since the value of this capacitor and the time between the voltage measurements are known, the impedance of the pacing vector can be readily calculated. Processes for measuring impedance are further described in U.S. Pat. No. 6,760,624 which is incorporated herein by reference.

Various other methods for determining impedance are known in the art and may be used to determine the impedance of the initial and/or alternate pacing vectors. The capture threshold for the alternate pacing vector is estimated 140 based on the measured threshold of the initial pacing vector, the measured impedance of the initial pacing vector, and the measured impedance of the alternate pacing vector.

Estimation of the capture threshold of the alternate pacing vector in accordance with some embodiments described herein, is based on the assumption that for a given pulse width, the capture threshold voltage for the initial pacing vector and the capture threshold voltage for the alternate pacing vector require an equal amount of current, energy or charge. The relationship between the capture threshold voltage and current for each pacing vector can be defined by Ohm's law as follows:

$$V_{th} = I_{th} Z \quad [1]$$

where $V_{th}$ is the capture threshold voltage of the pacing vector, $I_{th}$ is the capture threshold current of the pacing vector, and $Z$ is the impedance of the pacing vector.

For the initial pacing vector, the relationship between the capture threshold voltage and current may be expressed as:

$$V_{th\text{-}in} = I_{th\text{-}in} Z_{in} \quad [2]$$

where, $V_{th-in}$ is the capture threshold voltage of the initial pacing vector, $I_{th-in}$ is the capture threshold current of the initial pacing vector, and $Z_{in}$ is the impedance of the initial pacing vector.

For the alternate pacing vector, the relationship between the capture threshold voltage and current may be expressed as:

$$V_{th-ex} = I_{th-ex} Z_{ex} \quad [3]$$

where, $V_{th-ex}$ is the capture threshold voltage of the alternate pacing vector, $I_{th-ex}$ is the capture threshold current of the alternate pacing vector, and $Z_{ex}$ is the impedance of the alternate pacing vector.

As previously stated, in some embodiments, the capture threshold current of two pacing vectors having a common electrode is assumed to be about equal, or, $I_{th-in} = I_{th-ex}$.

The relationship between the alternate and initial capture threshold voltages may then be expressed as:

$$V_{th-ex} = \frac{V_{th-in}}{Z_{in}} Z_{ex} \quad [4]$$

By the processes outlined above $V_{th-n}$, $Z_{in}$, and, $Z_{ex}$ are measured parameters, and the capture threshold voltage may be estimated based on these measured parameters.

Figure 2:
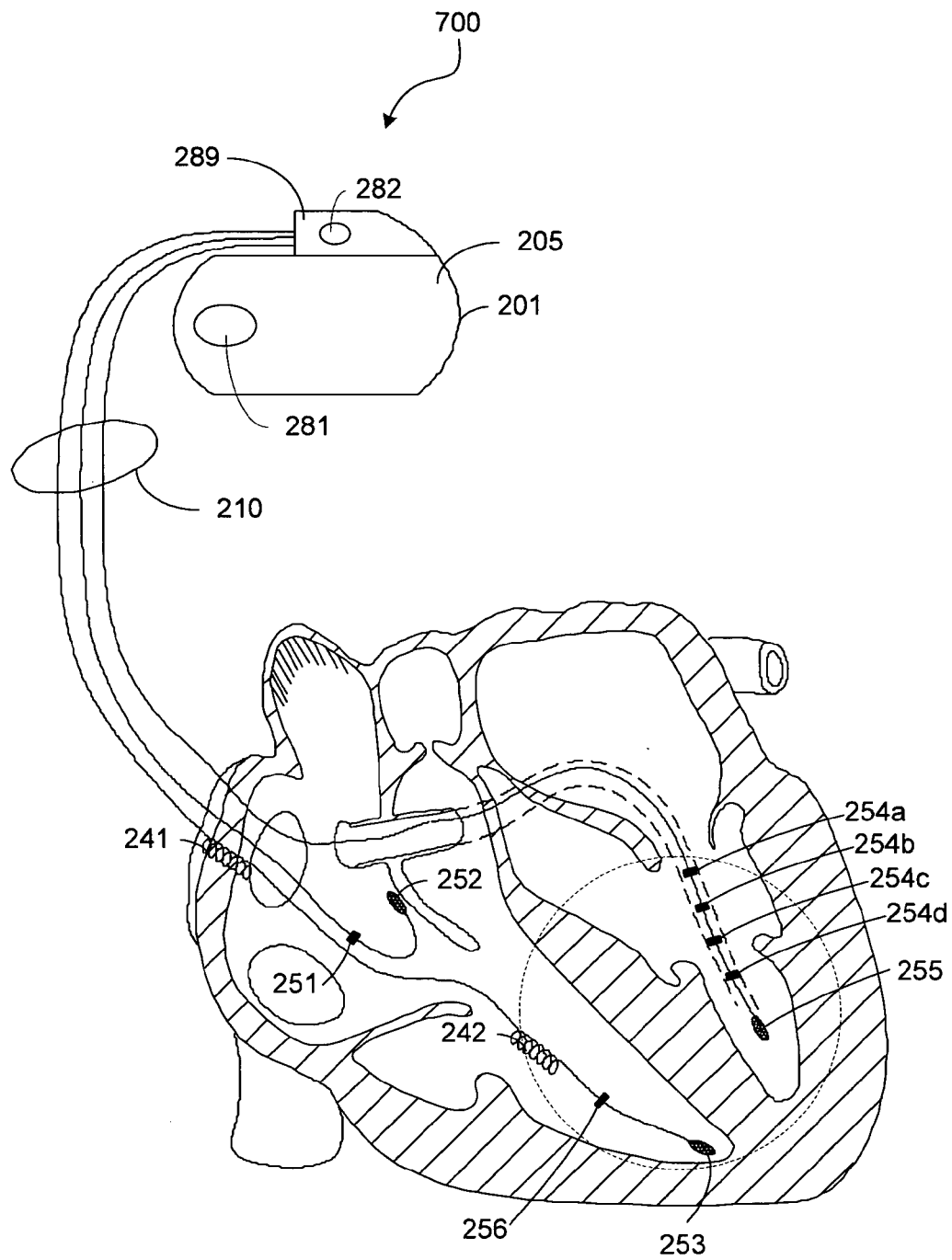
FIG. 2 is a therapy device incorporating circuitry capable of implementing capture threshold estimation techniques in accordance with embodiments of the invention.

The therapy device 200 illustrated in FIG. 2 employs circuitry capable of implementing the capture threshold estimation techniques described herein. The therapy device 200 includes cardiac rhythm management (CRM) circuitry enclosed within an implantable housing 201. The CRM circuitry is electrically coupled to an intracardiac lead system 210. Although an intracardiac lead system 210 is illustrated in FIG. 2, various other types of lead/electrode systems may additionally or alternatively be deployed. For example, the lead/electrode system may comprise and epicardial lead/electrode system including electrodes outside the heart and/or cardiac vasculature, such as a heart sock, an epicardial patch, and/or a subcutaneous system having electrodes implanted below the skin surface but outside the ribcage.

Portions of the intracardiac lead system 210 are inserted into the patient's heart. The lead system 210 includes cardiac pace/sense electrodes 251-256 positioned in, on, or about one or more heart chambers for sensing electrical signals from the patient's heart and/or delivering pacing pulses to the heart. The intracardiac sense/pace electrodes 251-256, such as those illustrated in FIG. 2, may be used to sense and/or pace one or more chambers of the heart, including the left ventricle, the right ventricle, the left atrium and/or the right atrium. The CRM circuitry controls the delivery of electrical stimulation pulses delivered via the electrodes 251-256. The electrical stimulation pulses may be used to ensure that the heart beats at a hemodynamically sufficient rate, may be used to improve the synchrony of the heart beats, may be used to increase the strength of the heart beats, and/or may be used for other therapeutic purposes.

The lead system 210 includes defibrillation electrodes 241, 242 for delivering defibrillation/cardioversion shocks to the heart.

The left ventricular lead 205 incorporates multiple electrodes 254a-254d and 255 positioned at various locations within the coronary venous system proximate the left ventricle. Stimulating the ventricle at multiple locations in the left ventricle or at a single selected location may provide for increased cardiac output in a patients suffering from congestive heart failure (CHF), for example, and/or may provide for other benefits. Electrical stimulation pulses may be delivered via the selected electrodes according to a timing sequence and output configuration that enhances cardiac function. Although FIG. 2 illustrates multiple left ventricle electrodes, in other configurations, multiple electrodes may alternatively or additionally be provided in one or more of the right atrium, left atrium, and right ventricle.

Portions of the housing 201 of the implantable device 200 may optionally serve as one or multiple can 281 or indifferent 282 electrodes. The housing 201 is illustrated as incorporating a header 289 that may be configured to facilitate removable attachment between one or more leads and the housing 201. The housing 201 of the therapy device 200 may include one or more can electrodes 281. The header 289 of the therapy device 200 may include one or more indifferent electrodes 282. The can 281 and/or indifferent 282 electrodes may be used to deliver pacing and/or defibrillation stimulation to the heart and/or for sensing electrical cardiac signals of the heart.

Communications circuitry is disposed within the housing 201 for facilitating communication between the CRM circuitry and a patient-external device, such as an external programmer or advanced patient management (APM) system. The therapy device 200 may also include sensors and appropriate circuitry for sensing a patient's metabolic need and adjusting the pacing pulses delivered to the heart to accommodate the patient's metabolic need.

In certain embodiments, the therapy device 200 may include circuitry for detecting and treating cardiac tachyarrhythmia via defibrillation therapy and/or anti-tachyarrhythmia pacing (ATP). Configurations providing defibrillation capability may make use of defibrillation coils 241, 242 for delivering high energy shocks to the heart to terminate or mitigate tachyarrhythmia.

CRM devices using multiple electrodes, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-electrode pacemaker has the capability of switching the output of pacing pulses between selected electrodes or groups of electrodes within a heart chamber during different cardiac cycles.

Figure 3:
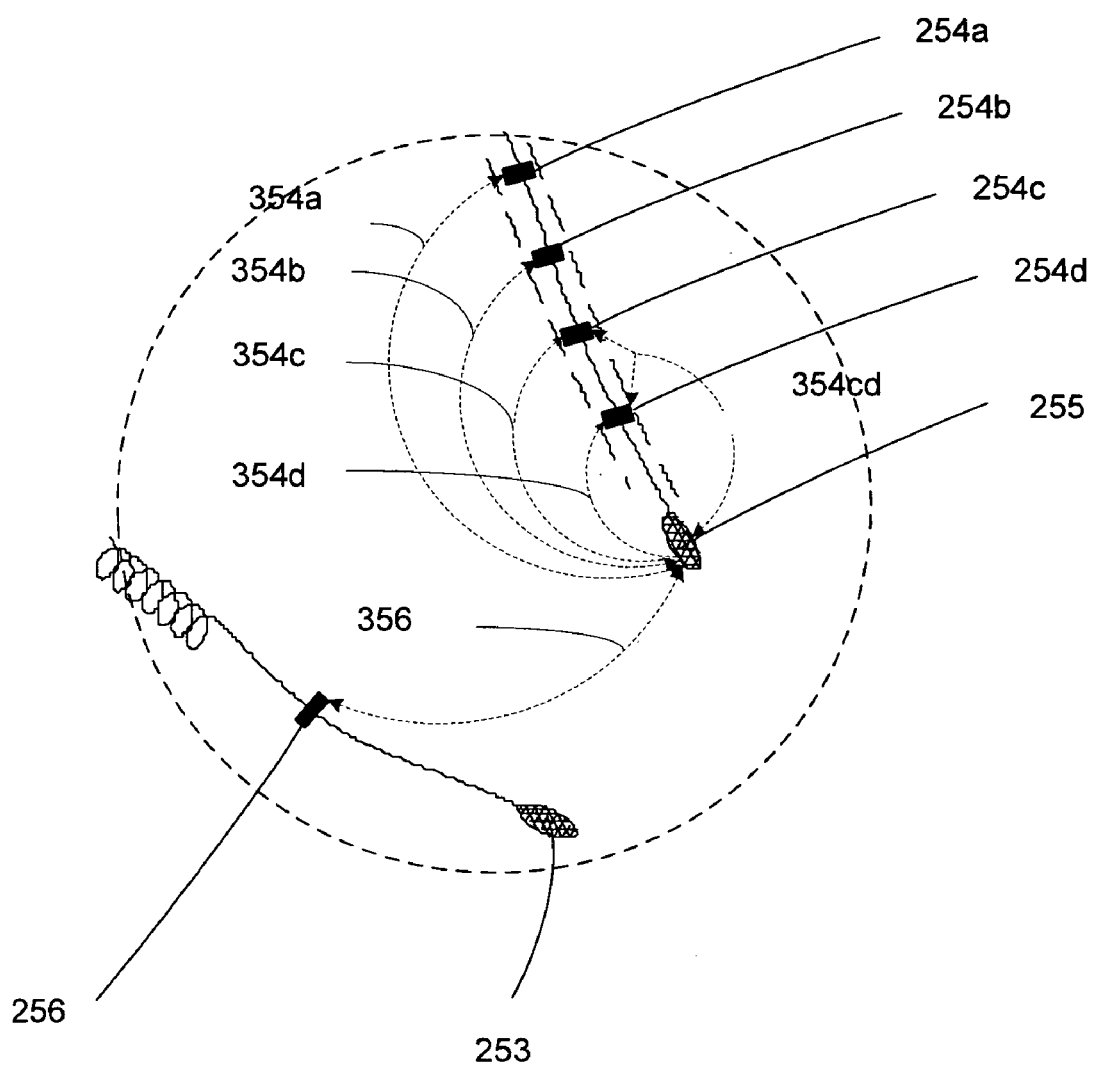
FIG. 3 shows an enlarged view of various pacing vectors that may be used in connection with estimation of capture thresholds in accordance with embodiments of the invention.

The capture threshold for various alternate pacing vectors may be estimated as described above based on measured capture threshold values and measured impedances. FIG. 3 illustrates an enlarged view of the area delineated by the dashed line circle in FIG. 2. FIG. 3 illustrates various pacing vectors 354a, 354b, 354c, 354d, 354cd, 356 that may be used to deliver pacing pulses. Each of the pacing vectors 354a, 354b, 354c, 354d, 354cd, 356 includes a common cathode electrode 255. Pacing vector 354a is defined between cathode electrode 255 and anode electrode 254a; pacing vector 354b is defined between cathode electrode 255 and anode electrode 254b; pacing vector 354c is defined between cathode electrode 255 and anode electrode 254c; pacing vector 354d is defined between cathode electrode 255 and anode electrode 254d; pacing vector 356 is defined between cathode electrode 255 and anode electrode 256. In some configurations, the pacing vector cathode, or the pacing vector anode, or both, may comprise multiple electrodes. For example, pacing vector 354cd includes cathode electrode 255 and anode electrodes 254c and 254d.

Figure 4:
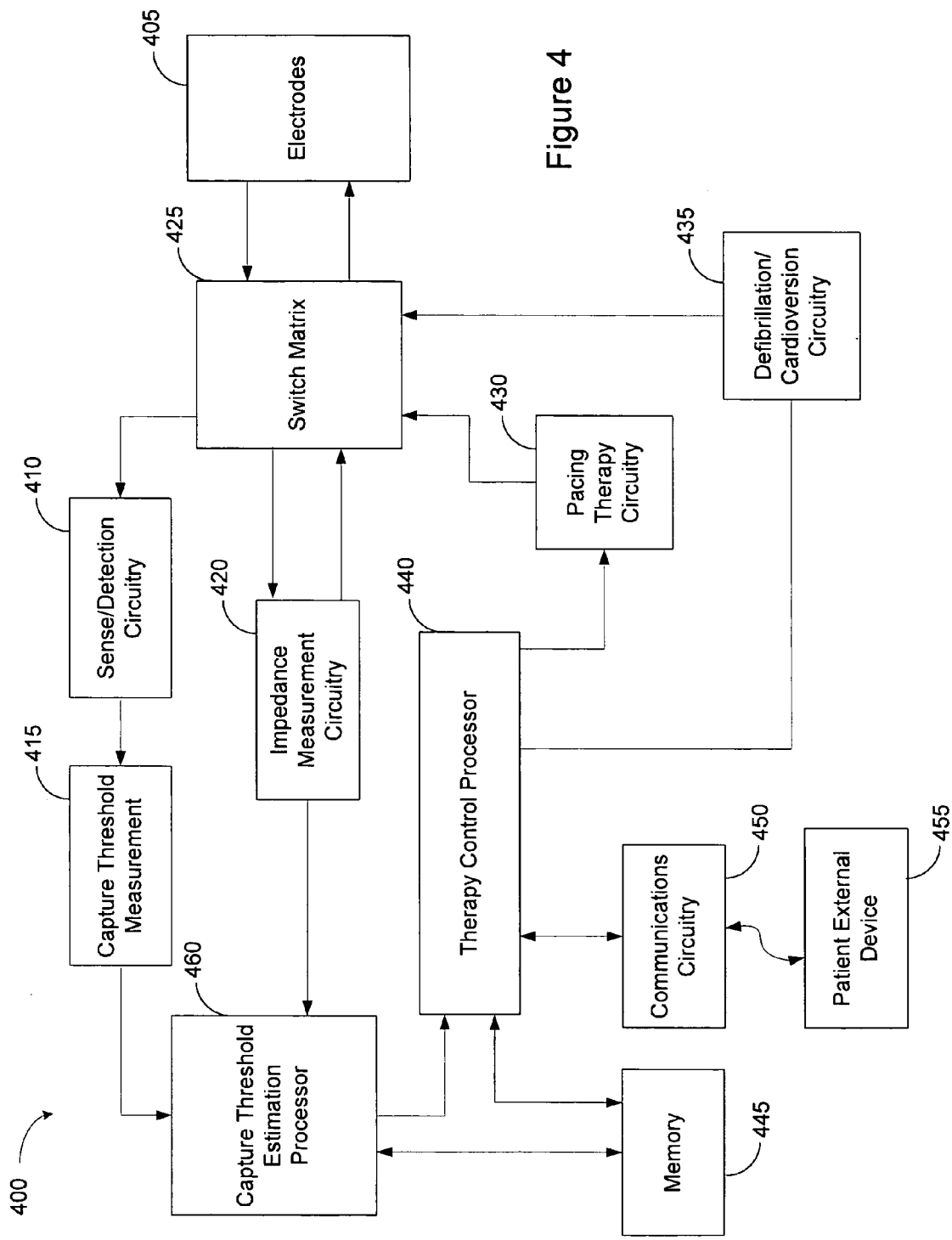
FIG. 4 is a block diagram of a system incorporating capture threshold estimation circuitry in accordance with embodiments of the invention.

FIG. 4 is a block diagram of a CRM device 400 that may incorporate circuitry for estimating capture thresholds in accordance with embodiments of the invention. The CRM device 400 includes pacing therapy circuitry 430 that delivers pacing pulses to a heart. The CRM device 400 may optionally include defibrillation/cardioversion circuitry 435 configured to deliver high energy defibrillation or cardioversion stimulation to the heart for terminating dangerous tachyarrhythmias.

The pacing and/or defibrillation pulses are delivered via multiple cardiac electrodes 405 are disposed at multiple locations within a heart. Certain pairs or groups of the electrodes 405 may be designated as alternate pacing vectors while other pairs or groups of electrodes 405 are designated as initial pacing vectors. Two or more electrodes may be disposed within a single heart chamber. The electrodes 405 are coupled to switch matrix 425 circuitry used to selectively couple electrodes 405 of various pacing vectors to capture threshold measurement circuitry 415, impedance measurement circuitry 420, and/or other components of the CRM device 400. The capture threshold measurement circuitry 415 is configured to measure the capture threshold of one or more initial pacing vectors, for example, by performing capture threshold tests, such as step-up, step-down, binary search, alternating amplitude capture threshold tests or other types of capture tests. The impedance measurement circuitry measures the impedance associated with various pacing vectors of interest, including the impedance of the one or more initial pacing vectors and the impedance of one or more alternate pacing vectors.

The measured capture threshold values and impedance values are used by a capture threshold estimation processor 460 to determine the capture threshold of the one or more alternate pacing vectors based on the measured values. The measured and estimated capture threshold values are passed to a therapy control processor 440. The therapy control processor 440 uses the measured and estimated capture threshold values to control pacing delivered to the heart via the initial and alternate pacing vectors, respectively.

A CRM device 400 typically includes a battery power supply (not shown) and communications circuitry 450 for communicating with an external programmer or other patient-external device 455. The CRM device 400 also includes a memory 445 for storing program instructions and/or data. In various configurations, the memory 445 may be used to store information related to capture threshold or impedance measurements.

In some embodiments, the capture threshold for the alternate pacing vector may be estimated based on multiple measurements of the initial pacing vector capture threshold or impedance. Multiple values of the capture threshold of one or more initial pacing vectors, the impedance of one or more initial pacing vectors and/or the impedance of an alternate pacing vector may be measured and stored in memory 445. In one implementation, the capture threshold estimation processor 460 retrieves the multiple measured values from memory 445 and determines an average value of one or more of multiple initial vector threshold measurements, multiple initial vector impedance measurements, and/or multiple measurements of the alternate vector impedance. The capture threshold estimation processor 460 may use one or more of the average values to estimate the capture threshold of the alternate vector. In other embodiments, a weighted average, or a most recent value of these parameters, may be used to estimate the alternate vector capture threshold.

Figure 5A:
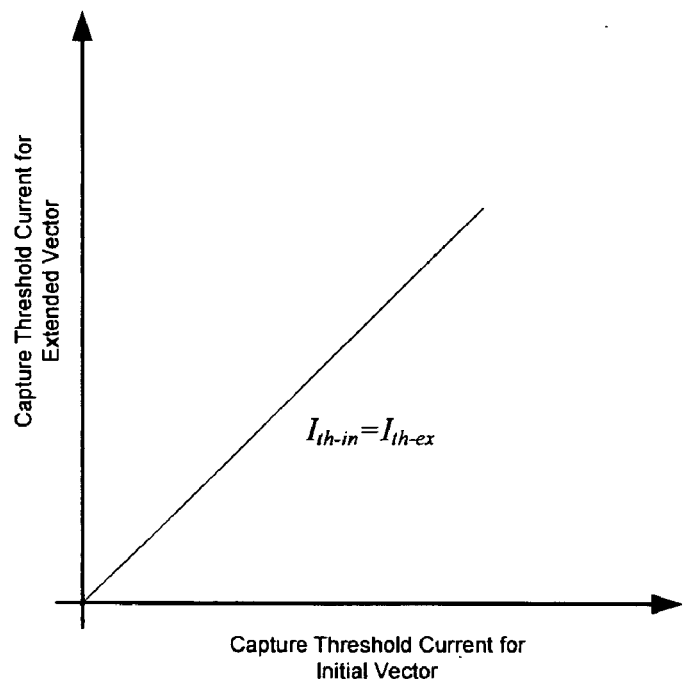
FIGS. 5A-5C are graphs showing relationships between the initial vector threshold current and the alternate vector threshold current that may be used in capture threshold estimation in accordance with embodiments of the invention.
Figure 5B:
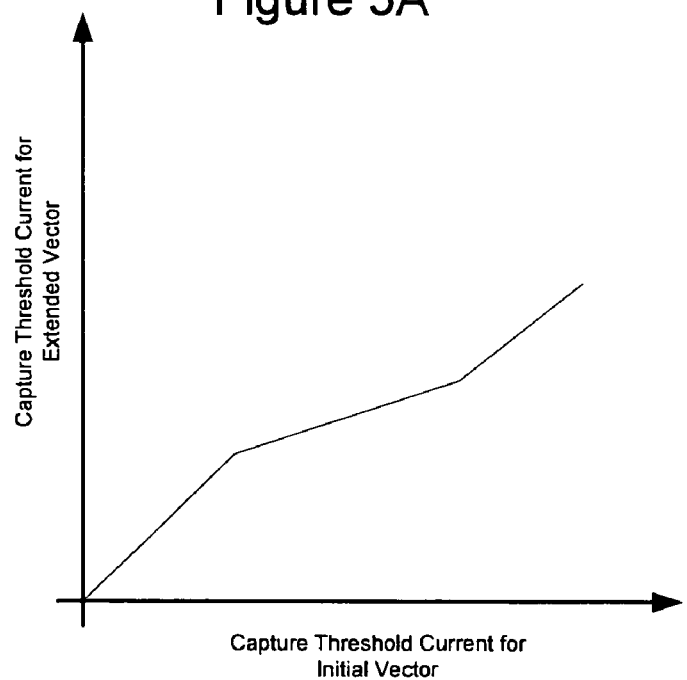
Figure 5C:
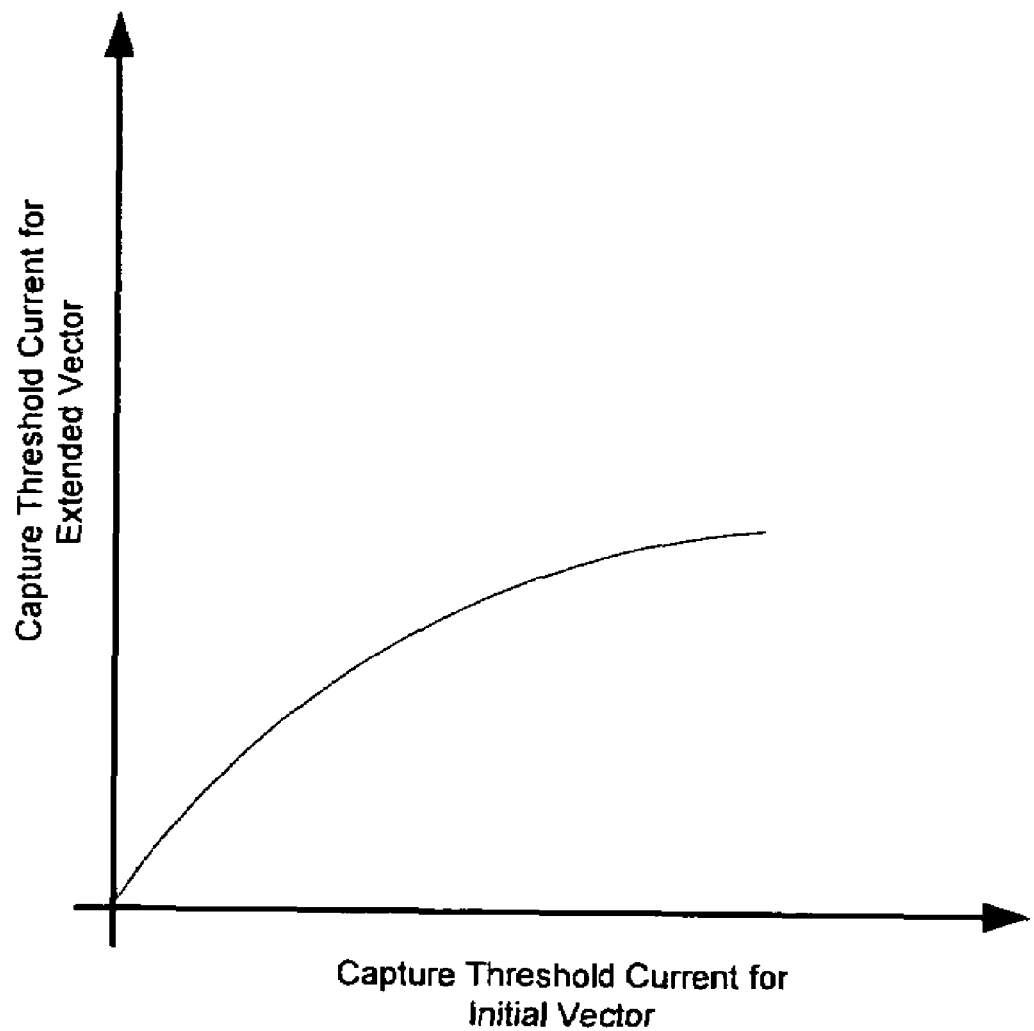

Estimation of an alternate vector capture threshold based on a measured capture threshold of an initial pacing vector sharing a common electrode with the alternate vector is based on a known or estimated relationship between the capture threshold current of the initial and alternate vectors. In the derivation of Equation 4 above, the capture threshold currents of the initial and alternate vectors were assumed to be linear and equal. An equal relationship between the capture threshold current of the initial vector and the capture threshold current of the alternate vector is illustrated in FIG. 5A. For some patients, the model of equal capture threshold currents may not be accurate over the full range of capture threshold currents. In these situations, models based on other relationships between the capture threshold currents for the initial and alternate vectors may be employed. For example, a linear, non-equal relationship between the capture threshold currents may be assumed. As further examples, illustrated by the graphs of FIGS. 5B and 5C, respectively, a piecewise linear relationship or a non-linear relationship between the capture threshold currents for the initial and alternate vectors may provide a more accurate estimation of the alternate vector capture threshold.

Figure 6:
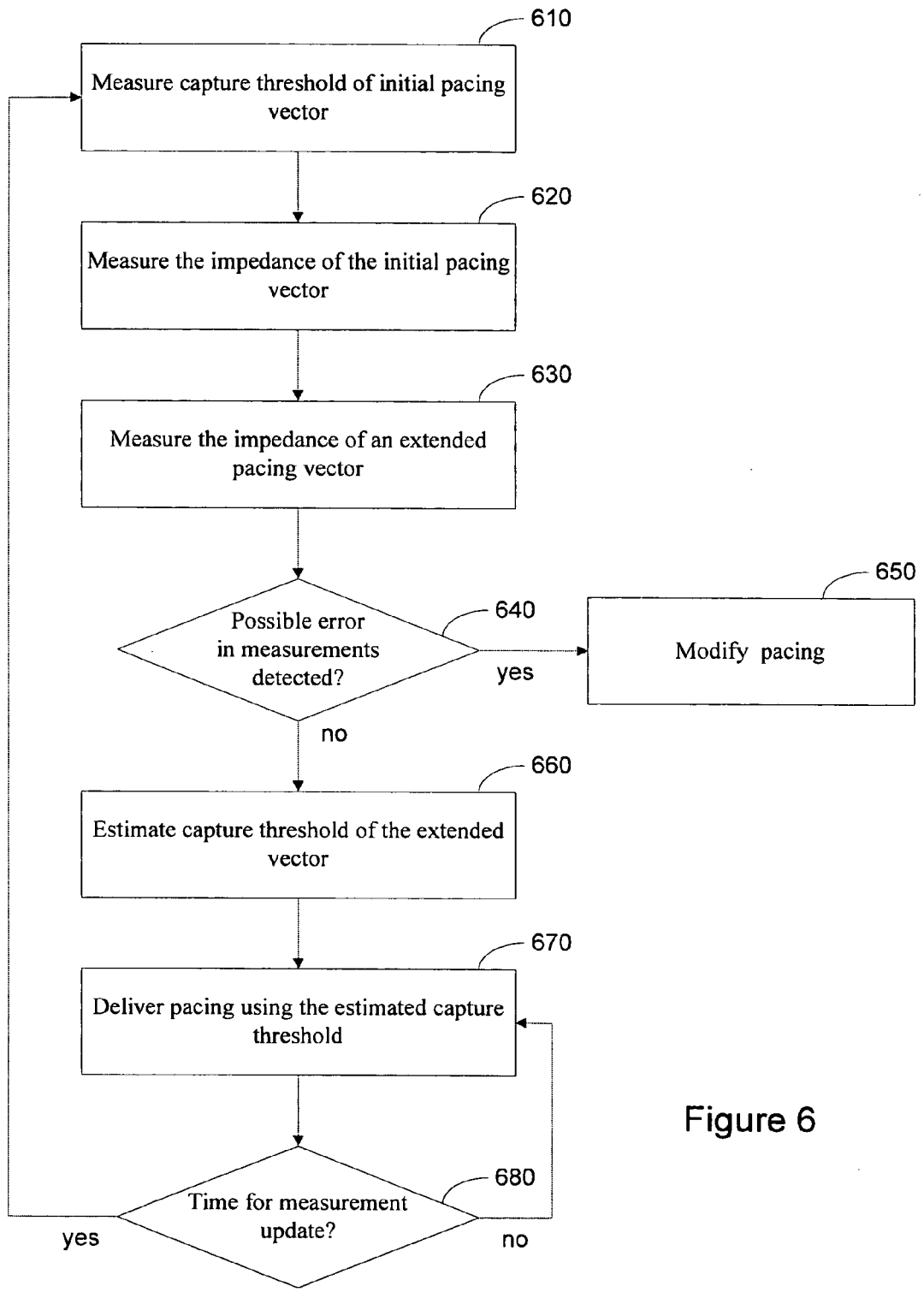
FIG. 6 is a flowchart illustrating a process for pacing via an alternate pacing vector using an estimated capture threshold value in accordance with embodiments of the invention.

Estimation of a capture threshold as opposed to direct measurement of the capture threshold may inject a certain amount of uncertainty into the pacing therapy delivered to the patient due to the possibility of error in the estimated value. For example, if an estimated capture threshold is based on a measured value that has high measurement to measurement variability, the possibility that the estimated capture threshold is erroneous is increased. An erroneous capture threshold value may not produce capture of the cardiac tissue and pacing support to the patient may be compromised. The flowchart of FIG. 6 illustrates a process for pacing via an alternate pacing vector using an estimated capture threshold value. The process illustrated in FIG. 6 includes steps to reduce the risk that an erroneously estimated capture threshold value is used in delivery of the pacing therapy. The capture threshold of an initial pacing vector, the impedance of the initial vector and the impedance of the alternate pacing vector are measured 610, 620, 630. The process checks to determine if there is a possible error in any of the measurements. For example, the possibility of erroneous measurements may be indicated by values that exhibit high measurement to measurement variability, detection of noisy signals, or other anomalies. If conditions indicating errors in any of the measured values are detected 640, pacing delivered via the alternate vector using the estimated capture threshold value may be disabled or pacing may be otherwise modified 650. An alert or other indicator may be generated to inform the patient or clinician of a possible error condition.

If conditions indicating errors in the measured values are not detected 640, the capture threshold of the alternate vector is estimated 660 based on the measured values. Pacing is delivered 670 via the alternate vector using the estimated capture threshold. Periodically 680, one or more of the capture threshold of the initial vector, the impedance of the initial vector and the impedance of the alternate vector may be re-measured and the alternate vector capture threshold estimation is updated.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for estimating capture thresholds for one or more alternate pacing vectors of an implantable cardiac device, comprising:
   measuring a capture threshold of at least one initial vector;
   measuring an impedance of the at least one initial pacing vector;
   measuring an impedance of at least one alternate vector, the at least one initial vector and the at least one alternate vector having an electrode in common, the common electrode having the same polarity for both the initial and alternate vectors; and
   estimating a capture threshold for the at least one alternate vector based on the measured capture threshold of the at least one initial vector, the measured impedance of the at least one initial vector, and the measured impedance of the at least one alternate vector.

2. The method of claim 1, wherein estimating the capture threshold comprises estimating the alternate vector capture threshold based at least in part on one or more of a most recent measurement of the initial vector capture threshold, a most recent measurement of the initial vector impedance, and a most recent measurement of the impedance of the alternate vector.

3. The method of claim 1, wherein estimating the capture threshold comprises estimating the alternate vector capture threshold based at least in part on an average value of at least one of multiple measurements of the initial vector capture threshold, multiple measurements of the initial vector impedance, and multiple measurements of the impedance of the alternate vector.

4. The method of claim 1, wherein estimating the capture threshold comprises estimating the capture thresholds of multiple alternate vectors based in part on the measured capture threshold of the at least one initial vector.

5. The method of claim 1, wherein estimating the capture threshold comprises estimating the capture threshold of the at least one alternate vector based in part on the measured capture thresholds of multiple initial vectors.

6. The method of claim 1, wherein estimating the capture threshold comprises estimating the alternate vector capture threshold based on an equal relationship between a capture threshold current, energy, or charge of the initial vector and a capture threshold current, energy, or charge of the alternate vector.

7. The method of claim 1, wherein estimating the capture threshold comprises estimating the alternate vector capture threshold based on a constant relationship between a capture threshold current, energy, or charge of the initial vector and a capture threshold current, energy, or charge of the alternate vector.

8. The method of claim 1, wherein estimating the capture threshold comprises estimating the alternate vector capture threshold based on a piecewise linear relationship between a capture threshold current, energy, or charge of the initial vector and a capture threshold current, energy, or charge of the alternate vector.

9. The method of claim 1, wherein estimating the capture threshold comprises estimating the alternate vector capture threshold based on a non-linear relationship between a capture threshold current, energy, or charge of the initial vector and a capture threshold current, energy, or charge of the alternate vector.

10. The method of claim 1, further comprising:
    detecting a possible error in at least one of the measured capture threshold of the initial vector, the measured the impedance of the initial vector, and the measured impedance of the alternate vector; and
    performing at least one of modifying pacing via the alternate vector and generating an alert responsive to the detected possible error.

11. A cardiac rhythm management system, comprising:
    electrodes electrically coupled to the heart, each pair of electrodes forming an initial vector or an alternate vector;
    capture threshold measurement circuitry configured to measure a capture threshold of at least one initial vector;
    impedance measurement circuitry configured to measure an impedance of the at least one initial vector and an impedance of at least one alternate vector, the at least one initial vector and the at least one alternate vector having an electrode in common, the common electrode having the same polarity in both the initial and alternate vectors; and
    a capture threshold estimation processor configured to estimate a capture threshold for the at least one alternate vector based on the measured capture threshold of the initial vector, the measured impedance of the initial vector, and the measured impedance of the alternate vector.

12. The system of claim 11, wherein the initial vector comprises at least one left ventricular electrode disposed in, on, or about a left ventricle and configured to sense or pace the left ventricle.

13. The system of claim 11, wherein the initial vector comprises at least one electrode disposed in, on, or about a right ventricle and configured to sense or pace the right ventricle.

14. The system of claim 11, wherein the alternate vector comprises at least one left ventricular electrode disposed in, on, or about a left ventricle and configured to sense or pace the left ventricle.

15. The system of claim 11, wherein the alternate vector comprises at least one right ventricular electrode disposed in, on, or about a right ventricle and configured to sense or pace the right ventricle.

16. The system of claim 11, wherein the initial vector comprises at least one electrode disposed in, on, or about an atrium and configured to sense or pace the atrium.

17. The system of claim 11, wherein the alternate vector comprises at least one electrode disposed in, on, or about an atrium and configured to sense or pace the atrium.

18. The system of claim 11, wherein the capture threshold estimation processor is configured to estimate the capture threshold of the alternate vector based at least in part on one or more of a most recent measurement of the capture threshold of the initial vector, a most recent measurement of the initial vector impedance and a most recent measurement of the alternate vector impedance.

19. The system of claim 11, wherein the capture threshold estimation processor is configured to estimate the capture threshold of the alternate vector based at least in part on an average value of at least one of multiple measurements of the capture threshold of the initial vector, multiple measurements of the impedance of the initial vector, and multiple measurements of the impedance of the second vector impedance.

20. The system of claim 11, wherein the capture threshold estimation processor is configured to estimate the capture threshold of a single alternate vector based in part on measured capture thresholds of multiple initial vectors.

21. The system of claim 11, wherein the capture threshold estimation processor is configured to estimate capture thresholds of multiple alternate vectors based in part on the measured threshold of the at least one initial vector.

22. The system of claim 11, wherein the capture threshold estimation processor is configured to estimate the capture threshold of the alternate vector based on an equal relationship between a capture threshold current, energy, or charge of the initial vector and a capture threshold current, energy, or charge of the alternate vector.

23. The system of claim 11, wherein the threshold parameter estimation processor is configured to estimate the capture threshold of the alternate vector based on a constant relationship between a capture threshold current, energy, or charge of the initial vector and a capture threshold current, energy, or charge of the alternate vector.

24. The system of claim 11, wherein the capture threshold estimation processor is configured to estimate the capture threshold of the alternate vector based on a piecewise linear relationship between a capture threshold current, energy, or charge of the initial vector and a capture threshold current, energy, or charge of the alternate vector.

25. The system of claim 11, wherein the capture threshold estimation processor is configured to estimate the capture threshold of the alternate vector based on a non-linear relationship between a capture threshold current, energy, or charge of the initial vector and a capture threshold current, energy, or charge of the alternate vector.

26. The system of claim 11, further comprising a therapy control processor configured to detect a possible error in at least one of the measured capture threshold of the initial vector, the measured impedance of the initial vector, and the measured impedance of the alternate vector, the therapy control processor configured to perform at least one of modifying pacing via the alternate vector and generating an alert responsive to the detected possible error.

27. A system for estimating capture thresholds for one or more alternate vectors, comprising:
   capture threshold measurement circuitry configured to measure a capture threshold of at least one initial vector;
   impedance measurement circuitry configured to measure an impedance associated with the initial vector and an impedance associated with at least one alternate vector; and
   means for estimating a capture threshold for the at least one alternate vector based on the measured capture threshold of the at least one initial vector, the measured the impedance of the at least one initial vector, and the measured impedance of the at least one alternate vector.

28. The system of claim 27, further comprising:
   means for detecting a possible error in at least one of the measured capture threshold of the initial vector, the measured the impedance of the initial vector, and the measured impedance of the alternate vector; and
   means for modifying pacing via the alternate vector responsive to the detected possible error.

29. The system of claim 27, further comprising means for estimating the capture threshold for a single alternate vector based in part on measured capture thresholds of multiple initial vectors.

30. The system of claim 29, further comprising means for estimating capture thresholds of multiple alternate vectors based in part on a measured capture threshold of the at least one initial vector.

* * * * *